(12) United States Patent
Stauch

(10) Patent No.: US 7,666,184 B2
(45) Date of Patent: Feb. 23, 2010

(54) PLANETARY ROLL SYSTEM, IN PARTICULAR FOR A DEVICE FOR EXTENDING BONES

(75) Inventor: Roman Stauch, Assamstadt (DE)

(73) Assignee: Wittenstein AG, Igersheim (DE)

( * ) Notice: Subject to any disclaimer, the term of this patent is extended or adjusted under 35 U.S.C. 154(b) by 433 days.

(21) Appl. No.: 10/569,665

(22) PCT Filed: Jul. 22, 2004

(86) PCT No.: PCT/EP2004/008195

§ 371 (c)(1),
(2), (4) Date: Feb. 24, 2006

(87) PCT Pub. No.: WO2005/027763

PCT Pub. Date: Mar. 31, 2005

(65) Prior Publication Data

US 2007/0015622 A1     Jan. 18, 2007

(30) Foreign Application Priority Data

Aug. 28, 2003 (DE) ............................... 103 40 025
May 24, 2004 (DE) ................... 20 2004 007 242 U

(51) Int. Cl.
*A61B 17/72* (2006.01)

(52) U.S. Cl. ....................................................... 606/63
(58) Field of Classification Search ................... 606/62, 606/63; 475/331
See application file for complete search history.

(56) References Cited

U.S. PATENT DOCUMENTS

| | | | | | |
|---|---|---|---|---|---|
| 3,178,967 | A | * | 4/1965 | Fritsch | 475/346 |
| 5,145,471 | A | * | 9/1992 | Meier-Burkamp | 475/331 |
| 5,704,938 | A | * | 1/1998 | Staehlin et al. | 606/62 |

FOREIGN PATENT DOCUMENTS

| | | |
|---|---|---|
| DE | 44 21 428 | 7/1995 |
| JP | 2001330087 | 11/2001 |
| WO | WO 01/81787 | 11/2001 |

\* cited by examiner

*Primary Examiner*—Eduardo C Robert
*Assistant Examiner*—Elana B Fisher
(74) *Attorney, Agent, or Firm*—Bachman & LaPointe, P.C.

(57) ABSTRACT

A planetary roll system, in particular for a device for extending bones. The system comprises two elements that can be displaced in opposition to one another and that are interconnected by at least one drive element. A hosing is designed to receive at least one planetary roll which comprises at least one radial cavity.

9 Claims, 3 Drawing Sheets

PLANETARY ROLL SYSTEM, IN PARTICULAR FOR A DEVICE FOR EXTENDING BONES

BACKGROUND OF THE INVENTION

The present invention relates to a planetary roller system, in particular for a device for extending bones, with two elements that can be moved in relation to one another and that are interconnected via at least one drive element.

Devices of this kind are known and commonly available on the market in a wide variety of formats and designs. They are used in particular also as a drive means for devices for extending bones. They can be inserted into a bone cavity or a medullary space of a bone, and distraction can take place after the bone has been cut through.

A disadvantage is that conventional planetary roller systems for distraction devices cannot take up or generate very high forces and cannot be exactly and precisely manufactured in miniature format. In addition, they must be able to be easily taken apart for cleaning, and, particularly when used in medical instruments, they must be able to be fitted very quickly and simply.

Specifically in the design of distraction devices having a very small cross section, planetary roller systems are used as drive systems whose cross sections have to have a very small diameter. In order to very high forces during distraction or movement of one element in relation to the other element, conventional planetary roller systems are not suitable as drive elements or drive units.

JP 2001 330087 A discloses a differential gear for a vehicle, in which three planetary rollers are mounted securely in a planetary roller cage.

A similar mounting of planetary rollers in planet carriers or cages is disclosed in DE 44 21 428 C1 and WO 01/81787 A.

The object of the present invention is to make available a planetary roller system, in particular for a device for extending bones, which overcomes the stated disadvantages and with which straightforward assembly and disassembly is possible in a simple, inexpensive and precise manner, and with which very high forces can be transmitted, the aim being for the planetary roller system to have very small diameters.

SUMMARY OF THE INVENTION

This object is achieved by the fact that a housing for receiving at least one planetary roller has at least one radial recess, and a receiving pocket is formed in each case at the front in the area of the recesses, said receiving pocket being arranged approximately centrally with respect to the recess in the circumferential surface and opening inwardly.

In the present invention, a housing for receiving the individual planetary rollers is formed which preferably has three radial recesses spaced apart from one another. The recesses are provided in a circumferential surface of a housing, corresponding receiving pockets being formed at the end of the respective recesses for the purpose of receiving shaft ends of planetary rollers for suitable bearing.

Three recesses are preferably provided at an angle of approximately 120° from one another in the circumferential surface of the housing. However, the scope of the present invention is also intended to cover the case where, for example, two opposite recesses or several recesses can be provided in the housing for the purpose of receiving planetary rollers. It is also conceivable for four radial recesses to be provided in the circumferential surface of the housing for the purpose of receiving the planetary rollers.

It is important in the present invention that the housing ensures that the individual planetary rollers are optimally mounted inside the recesses and inside the receiving pockets, and that simple assembly is therefore made possible by means of the housing. In this way, very high forces can be transmitted in a planetary roller system of this kind with the housing. In this way, the overall diameter of the planetary roller system can be made very small. This is also aided by the fact that the corresponding bridges are formed at an obtuse angle and thus enlarge the recesses, in particular in the inner area, such that the corresponding planetary rollers with greater diameter can be fitted. This likewise serves for optimal higher force transmission with reduction of the overall cross-sectional diameter of the planetary roller system.

BRIEF DESCRIPTION OF THE DRAWINGS

Further advantages, features and particulars of the invention will become evident from the following description of a preferred illustrative embodiment and from the drawing, in which.

DETAILED DESCRIPTION

Figure 1:
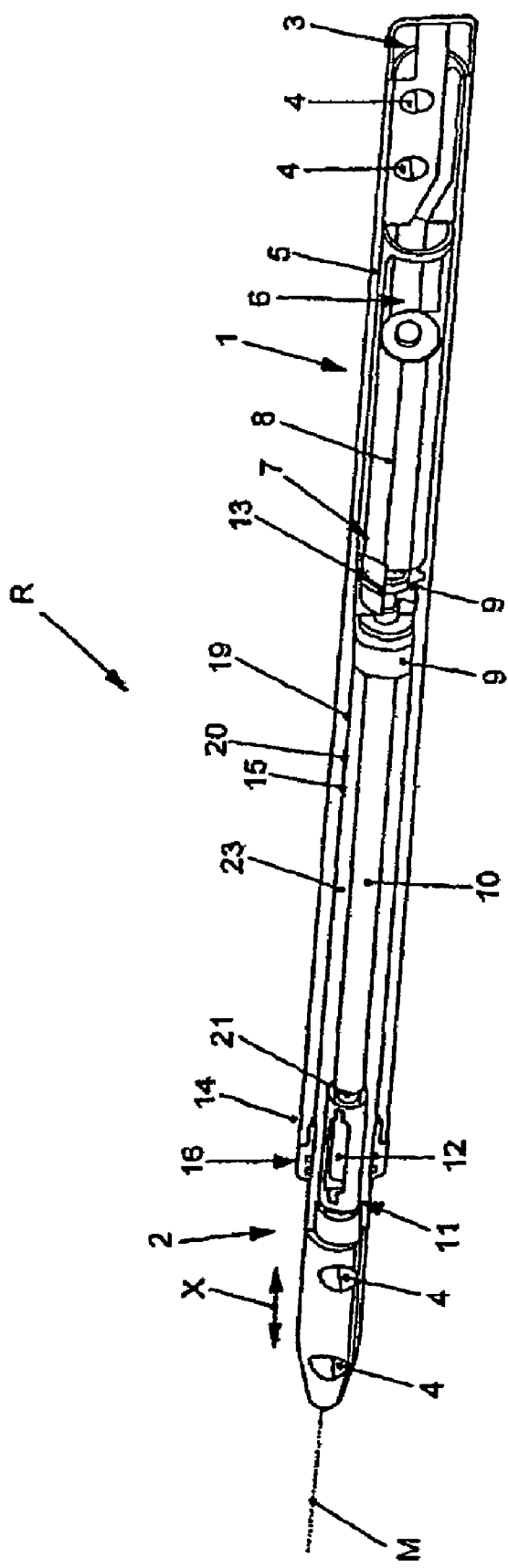
FIG. 1 shows a schematic and partial longitudinal section through the first element in the end area of a device for extending bones, with a planetary roller system.

According to FIG. 1, a device R according to the invention comprises a first element 1, and a second element 2 that is guided linearly and axially in said first element 1.

Integrated in the first element 1, particularly in the end area, there is an energy and/or data transmission element 3 which delivers the required energy and ensures energy transmission and bidirectional and contactless exchange of data. In the end area 19 of the element 1, there are also at least two radial locking bores 4 which serve to fix the device R for example in a bone that is to be extended. At the same time, the element 1 is secured against radial torsion relative to the bone during fixing.

The element 1 is preferably designed as a receiving sleeve 5 that comprises an electronics unit 6 (only symbolically indicated here) connected to the energy and/or data transmission element 3 and also to a drive element 7.

The drive element 7 comprises an electric motor 8 which sets a drive shaft 10 in a rotary movement via bearings 9 (only symbolically indicated here). Adjoining one end of the drive shaft 10 there is a planetary roller system 11 in which a plurality of planetary rollers 24 (symbolically indicated in FIG. 4) drive the individual planetary rollers 24 in rotation via the drive shaft 10, preferably configured as sun wheel 25. The planetary rollers 24 are fitted into corresponding recesses 12, which are described in more detail with reference to FIGS. 2, 3 and 4.

The electric motor 8 is preferably adjoined by a force sensor 13 for determining the axial forces of the shaft and also the torques, which force sensor 13 is in turn connected to the electronics unit 6.

Between the electric motor 8 and an end area 14 of the first element 1, the latter has a guide area 15 in its inside, said guide area 15 preferably having a cylindrical configuration.

In the end area 14, a guide element 16 is fitted on the element 1, this guide element 16 having an inner cross section 17 that corresponds approximately to an outer cross section 18 of the second element 2.

Inner cross section and outer cross section are preferably of polygonal configuration in cross section. In this way it is possible to avoid radial torsion of the element 2 guided in the guide area 15 of the element 1. It is able to move axially to and fro along a center axis M, but it cannot twist radially.

The element 2 is preferably configured almost completely as a polygonal profile with regard to its outer cross section.

However, in its end area 19, its cross section can have another outer contour 20 approximately corresponding to the guide area 15 of the first element 1.

The inside of the element 2, which is preferably configured as a crown wheel 26 (see FIG. 4), is preferably configured as rotary thread which interacts with the planetary roller system 11, in particular with the planetary rollers 24.

By means of suitable driving of the drive shaft 10 and sun wheel 25, the element 2 can move out of the element 1 in the direction of the double arrow X, along a center axis M indicated in FIG. 1.

The element 2 can be moved axially out of the element 1 until the end area 19 of the element 2 abuts internally against the guide element 16.

In this way it is possible to ensure a very substantial travel of the element 2 relative to the element 1.

In the present invention it is important that the substantial travel can also be achieved by the fact that the element 2 can be moved out axially in relation to the element 1 with absolute precision under very high forces via the planetary roller system 11, the element 2 being guided via the guide element 16 such that it cannot twist radially relative to the element 1.

However, the scope of the present invention is intended also to cover the case where the element 2 for example is not guided inside the element 1, but instead engages as an outer sleeve over the latter and receives the element 1 inside it and guides it in a manner secure against torsion. In this case, for example, the planet carrier 12 can lie outside the end area 14 of the element 1 and mesh with a corresponding inner thread 21 of the element 2.

The scope of the present invention is also intended to cover the case where, for example, the cross section of the end area 19 of the element 2 has a round, polygonal, many-cornered or other configuration in cross section, in order to ensure axial and radial guiding relative to the element 1, in which case a securing against torsion is not absolutely essential, because said securing against radial torsion can be ensured via the guide element 16 between elements 1 and 2.

Between the end area 19 and the guide element 16, a receiving space 23 for accommodating sensors, force sensors, displacement sensors or the like can be provided inside the guide area 15.

Figure 2:
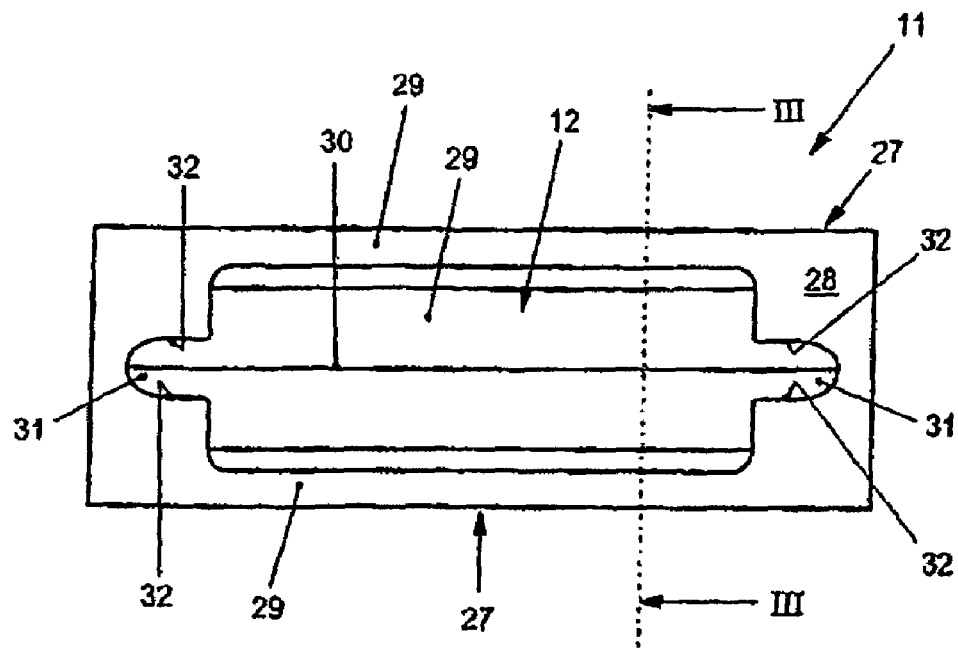
FIG. 2 shows a schematic plan view of an essential part of the planetary roller system.

In the illustrative embodiment according to FIG. 2, a housing 27 is shown which has an approximately cylindrical configuration and has a plurality of radial recesses 12 in a circumferential surface 28.

Between the individual radial recesses, individual bridge elements 29 are formed from the circumferential surface 28 and enclose an obtuse angle β, and a bridge apex 30 is oriented toward the center axis M.

Figure 3:
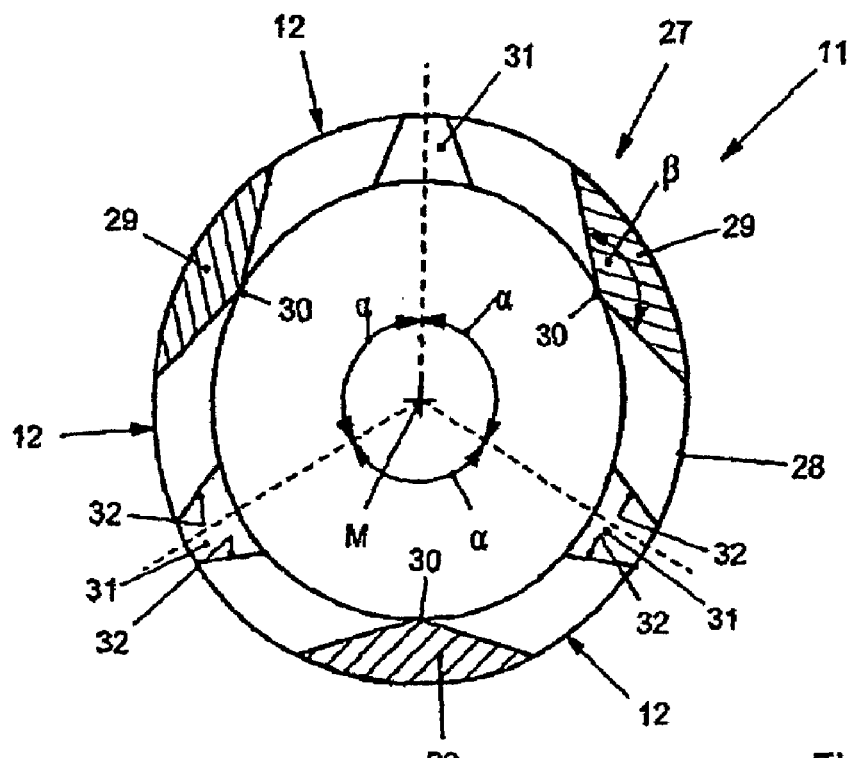
FIG. 3 shows a schematic cross section through a housing of the planetary roller system along line III-III in FIG. 2.
Figure 4:
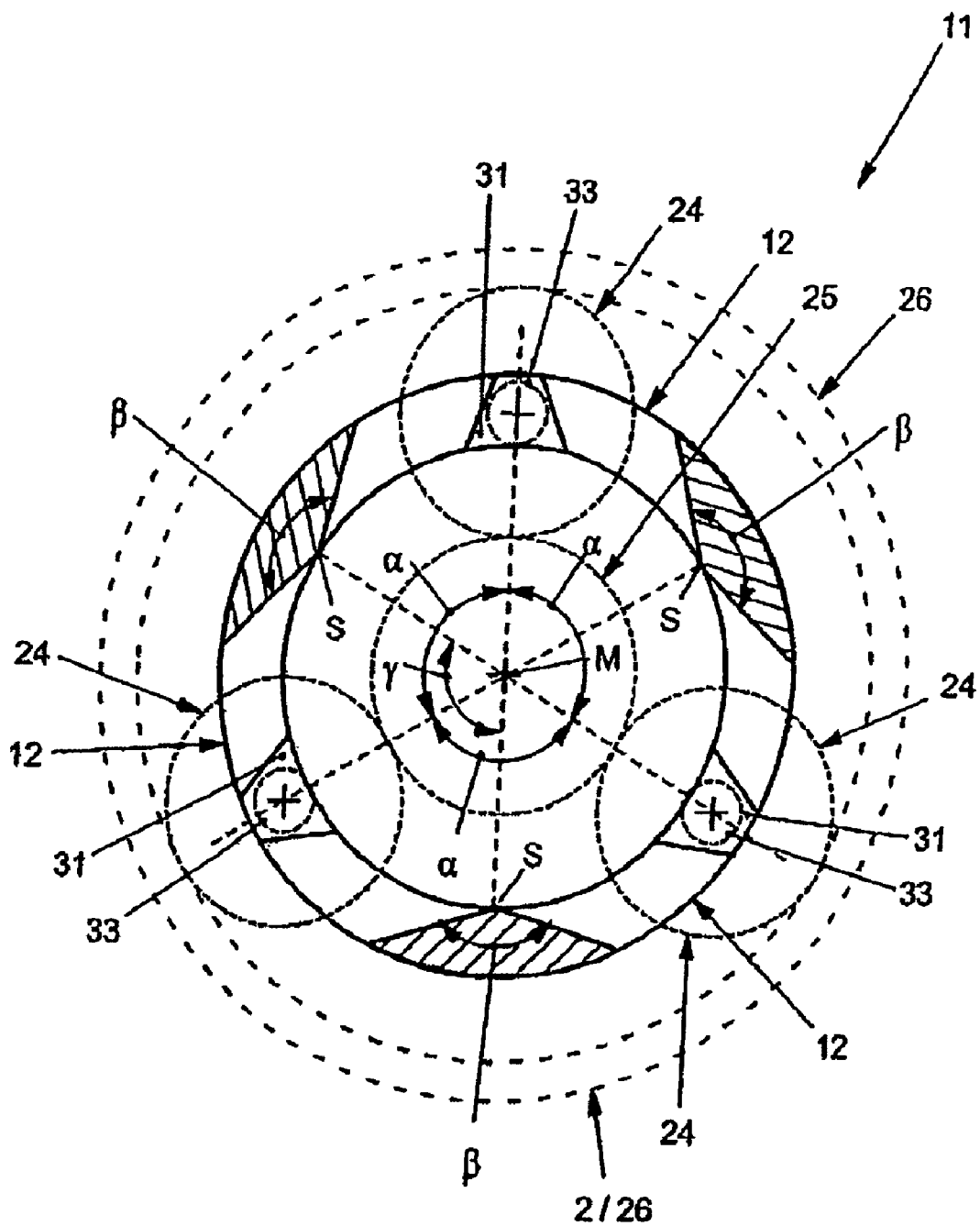
FIG. 4 shows a schematic cross section through the housing of the planetary roller system, with indicated planetary rollers, sun wheel and crown wheel.

As is indicated in FIGS. 3 and 4, the respective bridge apices 30 and the bridge elements 29 enclose an angle γ of approximately 120° relative to one another.

A recess 12 is formed in each case between the respective bridges 29, and the individual recesses 12 in end areas in the circumferential surface 28 of the housing 27 have receiving pockets 31, as is indicated in particular in FIG. 2. Inside walls 32 of the receiving pockets 31 can be oriented parallel to one another, or, as is indicated in particular in FIG. 3, they can be configured widening conically inward toward the center axis M, thus serving to support a shaft end 33 of the planetary roller 24. In this way, the planetary roller 24 can bear inside the receiving pockets 31.

However, the scope of the invention is also intended to cover the embodiment in which the inside walls 32 can be oriented parallel to one another.

The respective recesses 12 and receiving pockets 31 are arranged or spaced apart relative to one another at an angle α preferably of approximately 120° in relation to the center axis M.

When three planetary rollers 24 are fitted into the respective recesses 12 and receiving pockets 31, they are able to be engaged centrally by the drive shaft 20 or a sun wheel 25 and interact with a crown wheel 26 in order to move the two elements 1 and 2 linearly in relation to one another.

The invention claimed is:

1. A device for extending bones comprising:
a first element, a second element and a drive element interconnecting the first element and the second element for moving the first and second elements relative to one another for extending a bone;
said first element has at one end thereof an energy and/or data transmission element which delivers the required energy to an electronics unit which is connected to the drive element;
said second element has at one end thereof means for fixing the second element to a bone that is to be extended;
said drive element is connected to a drive shaft at one end thereof and imparts rotary movement thereto, said drive element comprises a planetary roller system received in a housing, said planetary roller system having at least one planetary roller, the housing has at least one radial recess formed in a circumferential surface of the housing, the at least one radial recess having an end face formed with a receiving pocket for receiving the at least one planetary roller of the planetary roller system.

2. The device as claimed in claim 1, wherein the housing has a cylindrical configuration, and the at least one radial recess comprises three or more radial recesses spaced apart from one another at an angle (α) of approximately 120°, and provided in the circumferential surface of the housing.

3. The device as claimed in claim 2, wherein bridge elements are formed between the respective three or more radial recesses.

4. The device as claimed in claim 3, wherein the bridge elements enclose an obtuse angle (β), and a bridge apex (S) is oriented toward a center axis (M) of the housing.

5. The device as claimed in claim 3, wherein the bridge elements are formed relative to one another from the circumferential surface of the housing.

6. The device as claimed in claim 3, wherein the bridge elements are spaced apart from one another by an angle (γ) of approximately in each case 120°.

7. The device as claimed in claim 1, wherein said receiving pocket is defined in part by inside walls, said inside walls of the receiving pocket are oriented parallel to one another.

8. The device as claimed in claim 1, wherein said receiving pocket is defined in part by inside walls, said inside walls of the receiving pocket are configured widening conically toward the at least one radial recess.

9. The device as claimed in claim 7 or 8, wherein corresponding shaft ends of the at least one planetary roller engage in the receiving pocket of the at least one radial recess, and the at least one planetary roller is mounted rotatably therein in the circumferential surface and in the housing.

* * * * *

UNITED STATES PATENT AND TRADEMARK OFFICE
CERTIFICATE OF CORRECTION

PATENT NO.      : 7,666,184 B2
APPLICATION NO. : 10/569665
DATED           : February 23, 2010
INVENTOR(S)     : Roman Stauch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 595 days.

Signed and Sealed this

Fourth Day of January, 2011

David J. Kappos
*Director of the United States Patent and Trademark Office*